US007289011B2

(12) United States Patent
Tan

(10) Patent No.: US 7,289,011 B2
(45) Date of Patent: Oct. 30, 2007

(54) ANIMAL PILL MAGNET HAVING SINGLE POLARITY

(75) Inventor: Li Ming Tan, Zibo (CN)

(73) Assignee: Animal Supplies International, Inc., Modesto, CA (US)

( * ) Notice: Subject to any disclaimer, the term of this patent is extended or adjusted under 35 U.S.C. 154(b) by 37 days.

(21) Appl. No.: 11/137,836

(22) Filed: May 25, 2005

(65) Prior Publication Data

US 2006/0266370 A1 Nov. 30, 2006

(51) Int. Cl.
*H01F 7/02* (2006.01)
*A61M 37/00* (2006.01)

(52) U.S. Cl. .......................................... 335/306; 600/12

(58) Field of Classification Search ................ 335/306; 600/12

See application file for complete search history.

(56) References Cited

U.S. PATENT DOCUMENTS

| | | | | |
|---|---|---|---|---|
| 2,613,246 | A * | 10/1952 | Spodig | 335/305 |
| 2,753,870 | A | 7/1956 | Muffly | |
| 2,799,274 | A | 7/1957 | Eisenhut | |
| 2,853,075 | A | 9/1958 | Hoffman et al. | |
| 3,005,458 | A | 10/1961 | Brook et al. | |
| 3,187,239 | A | 6/1965 | Rosenberger et al. | |
| 4,303,062 | A | 12/1981 | Vars | |
| 4,544,904 | A | 10/1985 | Tarachand | |
| 4,749,978 | A | 6/1988 | Imamura et al. | |
| 4,810,987 | A | 3/1989 | Liebthal et al. | |
| 4,888,068 | A | 12/1989 | Tokunaga et al. | |
| 4,992,768 | A | 2/1991 | Mozis et al. | |
| 5,096,763 | A | 3/1992 | Ogata et al. | |
| 5,128,644 | A | 7/1992 | Nellessen | |
| 5,663,701 | A | 9/1997 | Kaura | |
| 5,905,425 | A | 5/1999 | Dalby et al. | |
| 6,357,446 | B1 | 3/2002 | Taparia | |
| 6,374,670 | B1 | 4/2002 | Spelman et al. | |
| 6,905,596 | B2 * | 6/2005 | Chu | 210/222 |

* cited by examiner

*Primary Examiner*—Ramon M. Barrera
(74) *Attorney, Agent, or Firm*—Jones Day

(57) ABSTRACT

An improved animal pill or cow magnet that is inserted into the stomach of a bovine animal to attract and hold tramp metal ingested by the animal so as to prevent the adverse condition commonly referred to as “hardware disease.” The disclosed device has at least a pair of NdFeB magnets separated by a carbon steel section within the stainless steel outer casing. The resulting magnetic field for the overall animal pill magnet has a single polarity, which by design can be either N or S.

11 Claims, 3 Drawing Sheets

ANIMAL PILL MAGNET HAVING SINGLE POLARITY

BACKGROUND OF THE INVENTION

This invention relates to animal pill magnets that are routinely placed in the stomachs of bovine animals to prevent the adverse condition that is commonly referred to as Hardware Disease. More specifically, this invention pertains to such an animal pill magnet that exhibits a single polarity.

Bovine animals, particularly cattle, forage hastily without chewing their food initially. Generally, whatever goes into a cow's mouth while it is feeding gets swallowed and enters the animal's rumen. Later, the previously-ingested material is regurgitated, and the animal "chews its cud." This process is believed to have evolved over many years so that the bovine animal in the wild could quickly ingest huge amounts of grass in a short amount of time, thereby limiting the amount of time that its head, eyes and ears were in a lowered position and the animal was more vulnerable to predator attacks. Later, the animal could complete the digestive process by chewing its cud with its head, eyes and ears in an upright position, on the lookout for advancing predators. While such evolutionary survival traits are not needed today in the typical dairy farm, feed lot, or cattle ranch, the modem bovine still has this quick-foraging trait which served the animal so well in the wild, although that trait now presents a problem for the modern cow confined in spaces that include man-made debris. Specifically, in this process of hastily feeding, the cow, whether in a dairy or feed lot being fed prepared feed in a trough or other confined space, or in open pasture grazing over a wider area, has a tendency to ingest not just the intended grass, hay or other foodstuffs, but also to ingest the small metal objects ubiquitously found on most farms, such as nails, staples, and bits of bailing or barbed wire. These things are often referred to as tramp iron. Because the animal does not chew during the initial eating process, these items are not rejected by the cow at that time. Also, because of their weight, size and shape, these items are not usually regurgitated later as part of the cud, so they cannot be rejected then. Rather, these foreign objects remain in the cow's digestive tract, where they can cause problems.

The primary problem results when the bits of tramp iron fall to the floor of the animal's rumen, and then get pushed forward and lodged in the honeycombed walls of the animal's recticulum. The powerful churning and contractions of the animal's digestive track can in some instances cause the sharp-edged and sharp-ended bits of metal to irritate and inflame the side walls of the animal's stomach. In some instances, the wire or nail may actually be caused to puncture the stomach wall. Given the close proximity of other organs (such as the heart and lungs), that can lead to the metal's damaging those other organs. Or, the puncture in the stomach wall can lead to leaking digestive juices that can cause infections.

This condition is generally referred to as Hardware Disease. In its least damaging manifestation, a dairy cow's milk product may fall off significantly, or a feed animal being raised for eventual slaughter may experience weight loss instead of the desired weight gain. In more serious manifestations, the infected animal can die from damage caused to an internal organ, from internal infection or even from starvation, as an animal afflicted with Hardware Disease may actually stop eating altogether. Sometimes, surgery to remove the offending material may be required.

For these reasons, cattle ranchers and dairy farmers take steps to prevent the animal's ingestion of tramp iron. For example, feed mills will actually install powerful magnets in a late processing stage so that tramp iron is culled from the feed being milled before it is given to the animals. Keeping the feeding areas free of tramp iron is also a goal. These things, while effective to a degree, however, have not been found to be completely effective, and have not eliminated Hardware Disease.

Indeed, Hardware Disease has plagued cattle ranchers, feed lot operators and dairy farmers for years. Years ago it was discovered that while it was not feasible to prevent all cows from ingesting tramp iron all the time, such that cows were inevitably going to be eating some tramp iron and other metal objects, the advent of Hardware Disease could be substantially reduced by causing the animal to ingest small, powerful magnets that were sufficiently heavy that they would remain in the bottom of the cow's stomach for the animal's lifetime. The magnets would attract and hold the small bits of metal debris as they were ingested, keeping the metal in the bottom portions of the animal stomach where it was much less likely to cause irritation, inflammation or a puncture wound to the stomach wall. Over time, the stomach's acids will actually dissolve some of the metal. For example, a typical iron nail can be dissolved in about 6 months.

So that the magnets would not themselves cause problems, it has been known in the art that the exterior surface of the magnet should be very smooth. Because of the caustic nature of the animal's digestive juices, it has also been known in the art that the magnets must be sheathed in a protective material, such as stainless steel or suitable plastic coating, that can withstand the caustic digestive juices.

In addition to administering a magnetic pill to the animal, some of the earlier patented devices directed to this disease were instruments that used retrievable magnets that could used to remove the offending material non-surgically. For example, U.S. Pat. No. 2,753,870, issued in 1956, discloses an "Instrument for Probing the Reticulum" in which a large magnet attached to a tether is introduced to the animal's stomach via the esophagus to retrieve and remove metal objects. As described in the '879 patent, it was already "common practice in the treatment of hardware disease to feed the animal a small magnet."

In U.S. Pat. No. 2,799,274, issued in 1957, a "Veterinary Evacuating Probe for Use on Cattle" is disclosed which the veterinary surgeon could insert through the esophagus into the animal's stomach to "feel" for, retrieve and remove foreign objects.

And in U.S. Pat. No. 2,853,075, issued in 1958, a "Rumen Trocar Extricator" is disclosed that, among other things, could be used to "successfully and satisfactorily introduce the magnet into the intended areas of the cow's stomach." As these references confirm, Hardware Disease has long plagued the bovine animal industry, and the use of magnets, either tethered so as to be retrievable, or specifically placed using a non-surgical instrument, or administered orally, in the treatment of that disease has long been known.

Notwithstanding the long use of magnets in this way, there has been a constant effort to improve the magnet in one way or another. Indeed, a rather large number of patents have been issued for these "cow magnets" (as they are sometimes called in addition to "animal pill magnets"). For example, one of the early patented devices was called a "Therapeutic Magnet" in U.S. Pat. No. 3,005,458, issued in 1958, which described the effects of Hardware Disease to be popularly known as "off feed," or "bloat," or "indigestion"

or "off production." The disclosed improved magnet had a particular shape (elongated with a dog-bone like cross section) and its ends were of opposite polarity.

In U.S. Pat. No. 3,187,239, issued in 1965 for a "Holding Magnet for Ferromagnetic Foreign Bodies in Ruminants," various drawbacks experienced with the prior art magnets were described, including that the metal objects that were held by the magnet were not always attached longitudinally, such that a "hedgehog" was formed around the magnet that could still puncture the animal's stomach wall. The improved magnet disclosed used the prior art N-S cylindrical magnet having opposite polarity at its ends, but encased the magnet in a "cage" of elongate bars that helped properly orient the metal objects attached to the magnet. This supposedly helped reduce the "hedgehog" effect.

In U.S. Pat. No. 4,303,062, issued in 1981 for a "Therapeutic Magnet," an improved magnet is disclosed which had a rectangular shape, and in which the opposite N-S polarities were on the opposite sides of the magnet (as opposed to its ends). The '062 patent discusses the problems associated with the use of magnets such as disclosed in U.S. Pat. No. 3,005,458. One such problem identified is that care had to be taken to ensure that two magnets are not administered to the same animal, as the two magnets would attach themselves to each other, N-end to S-end, thus shunting one another and greatly reducing the external magnetic field. The disclosed and claimed magnet used a core of "AlNiCo—V" material (AlNiCo means Aluminum-Nickel-Copper), a polymeric coating, and a prescribed length-to-width overall ratio, such that its pole faces were on the sides of the magnet having the greatest area.

In U.S. Pat. No. 4,749,978, issued in 1988 for a "Magnet for Catching Thereon Foreign Bodies Within Reticulum of Ruminant, and Method and Instrument for Manufacture Thereof," the problem of end-to-end attachment of multiple magnets in the cow's stomach was again cited, and the disclosed and claimed cow magnet had its magnetic N-S poles on selected side portions of the elongate device (as opposed to at its respective ends). The description of the prior art in the '978 patent also describes other drawbacks encountered with the typical cow magnet having N-S poles at its opposite ends.

In U.S. Pat. No. 4,992,768, issued in 1991, a cow magnet is disclosed having a stack of cylindrical permanent magnets with intermediate disk-like spacers of soft magnetic material, all of which are held in place by a central pin or rod which itself was of a soft magnetic material. This arrangement was believed to enhance the magnetic flux lines generated by the overall N-S ends of the composite device.

In U.S. Pat. No. 5,096,763, the problems with the conventionally used, rod-shaped AlNiCo magnets having magnetic poles at both end surfaces, are described. Also described are the prior art attempts to correct those problems by using a plurality of disc-shaped magnetic members having magnetic poles on each of their end surfaces, such that the resultant composite device has alternating N-S poles (up to 8) along its axial length. The disclosed improved magnet incorporated several ferrite disc magnets each having N-S polarity in order to achieve the desired alternating N-S polarity along the sides of the device.

In U.S. Pat. No. 5,663,701, issued in 1997, a "Stomach Debris Collecting Magnet" is disclosed that is described as being an improvement over the prior art by creating a magnetic "dead zone" intermediate of the two ends of the device, which the patent describes as enhancing the device's ability to create a "ball" of attracted metal that maximized the amount of material collected, and minimizes the risk that on end an attracted piece of metal would still puncture the stomach wall.

In U.S. Pat. No. 5,905,425, issued in 1999 for a "Cow Magnet," the preferred cow magnet is described as one having seven attributes: 1) sufficiently strong magnetic field; 2) non toxic to the cow; 3) able to withstand the corrosive stomach acids; 4) dimensioned so as not to pass through to the cow's intestines; 5) easily inserted down the cow's throat; 6) inexpensive to manufacture; and 7) configured so that the attracted metal will gather in a fashion that poses the least risk to the animal. The improved cow magnet disclosed comprises two elongate semi-circular ceramic magnets having a metal plate between them, all encased in a plastic outer coating.

And perhaps most recently, U.S. Pat. No. 6,357,446 B1 issued in 2002 for an "Animal Pill Magnet" having the usual elongate, cylindrical shape, and N-S poles at each end, in which the claimed improvement relates to the manner in which the two capsule halves are secured together.

As this brief review of some of the prior art patents on cow magnets shows, there has been a continuing attempt to improve a device that has been in common usage for over 50 years. As this review also shows, much of the attempts at improvement have been directed to the polarity of the device. For example, at least 25 years ago a problem with having a cow magnet with N-S polarity at its ends was described in that if two cow magnets were administered to the same animal, the two cow magnets would become attached end-to-end, reducing the magnetic field, and hence reducing the device's effectiveness. However, as the prior art also discloses, the preferred device has a shape, size and weight such that it remains in the bottom of the cow's stomach for its lifetime. Therefore, as the cow magnet attracts more and more material (creating the "ball" described above), the magnet's ability to attract and hold additional objects decreases. According, administering additional magnets to the same cow is commonplace. Indeed, the West Virginia University Veterinary Sciences Extension Service's admonition to veterinarians in the field on Hardware Disease is to "[j]ust remember that if enough metal is ingested the magnet will 'fill up'" such that the veterinarian should "[a]dminister a second magnet if signs resembling hardware disease are present." Yet, the most commonly used standard cow magnet today still has an AlNiCo magnet that has a different pole on each end. (See, for example, the cow magnets available at http://www.magneticsource.com or http://www.physlink.com). The metal that is attracted to one end of the magnet can become partially magnetized itself, and can be repelled by the other end, leading to the situation in which the magnet "holds" a wire segment (for example) at one end thereof, while the other end thereof can be "held" in an outwardly extending position that can damage or even puncture the stomach wall, even though one end of it is attached to the magnet. Therefore, after over 50 years of improvement, the problems with the traditional N-S polarity at the opposite ends of the typical cow magnet remain.

Thus, there still exists a need in the art for an improved animal pill (or cow) magnet that can attract and hold large quantities of metal debris without creating a puncture risk to the animal, and which can be administered repeatedly to the same cow without adversely affecting the efficacy of the device.

SUMMARY OF THE INVENTION

The improved cow magnet herein describes has a unique arrangement of interior NdFeB (Neodymium-Iron-Boron) magnets separated by carbon steel such that the resultant device exhibits a single polarity at each end, and that polarity can by design be either N or S. The resultant cow magnet thus can attract and hold more metal (as it attracts only and does not repel), and acts to bring the metal pieces it attracted into axial alignment so as to minimize extending sharp ends of the attached metal objects.

DESCRIPTION OF THE PREFERRED EMBODIMENT

Figure 5:
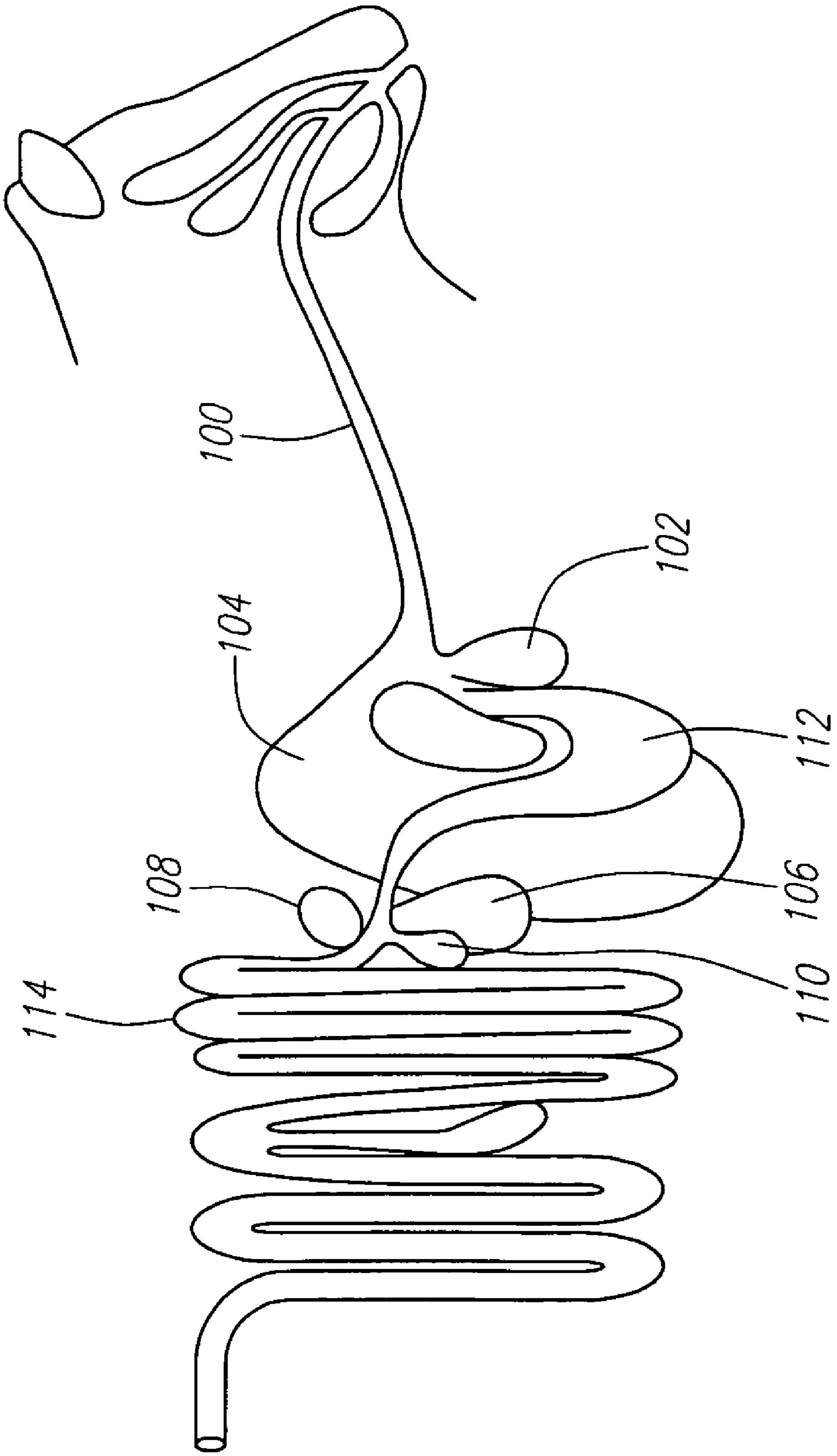
FIG. 5 is a schematic view showing the major anatomical components of a cow's digestive system of interest here.

The device of this invention is intended to be orally administered to a bovine animal and once administered, to permanently reside in the animal's reticulum, where it attracts and holds tramp iron that the animal ingests, thereby preventing the animal from contracting Hardware Disease. In order to understand this process, a diagram of the main anatomical components of a bovine digestive system of interest here are shown in FIG. 5. Beginning at the animal's head and mouth depicted at the right side of the diagram and moving to the left, the esophagus 100 leads to the animal's multi-compartment stomach including the reticulum 102 and the rumen 104. Although not shown on this diagram, the animals heart and lungs are located generally in the area adjacent to the reticulum 102. The animal's liver 106, pancreas 108, and gall bladder 110 are located adjacent the rumen 104, and to the abomasum 112, which leads to the small intestines 114. As this diagram shows, sharp-pointed or sharp-edged pieces of metal, once ingested by the cow, have many opportunities to cause problems for the animal. If the metal object is forced into the reticulum 102, it can puncture the reticulum wall and injure the heart or lungs. If the object is moved along the animal's digestive tract, it can puncture the intestines and perhaps injure the liver or other important internal organs.

Figure 1:
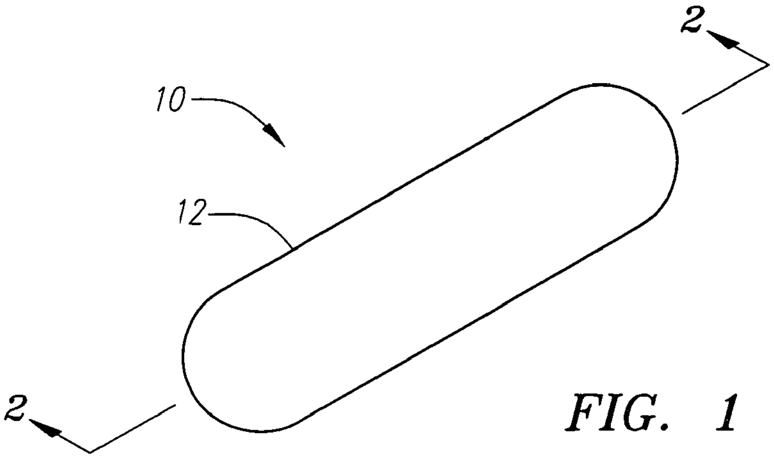
FIG. 1 is a perspective view showing the overall size and shape of the magnet.

Looking now at FIG. 1, it is seen that the overall animal or cow magnet 10 of the preferred embodiment of this invention has a traditional elongated, cylindrical shape that resembles a large pill or bolus. The preferred dimensions are approximately 3 inches in length and ½ inch in diameter, with rounded ends such that there are no sharp edges anywhere on its exterior.

Figure 2:
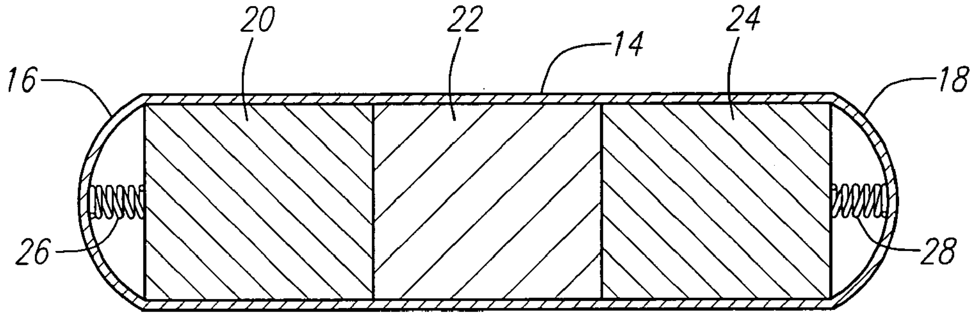
FIG. 2 is a cross-sectional side view showing the internal components of one embodiment.

Looking at FIG. 2, it is seen that this device has an outer casing 12 that encases various interior components. In the preferred embodiment, outer casing 12 is constructed entirely of stainless steel, and is comprised of a cylindrical sleeve portion 14 and two end caps 16 and 18. Of course, many other materials could be used for the outer casing 12, such as other metals or plastics that would be sufficiently resistant to corrosion from the animal's gastric juices. The overall shape of the device, while preferable a cylinder with rounded ends, could be of any other shape and size. The only limiting aspect is that the design must be one which the animal can be forced to swallow, and which does not its pose a danger to the animal stomach walls.

FIG. 2 also discloses a preferred embodiment in which the interior space of the overall magnet 10 comprises a first NdFeB (Neodymium-Iron-Boron) magnet 20, and intermediate carbon steel section 22; and a second NdFeB magnet 24, all being of approximately the same size (hereinafter this assembly of the steel section 22 sandwiched between magnets 20 and 24 is referred to as to the "magnet/steel assembly"). As depicted here, each of the magnets 20 and 24 and the steel section 22 are shaped as cylindrical segments, having an exterior diameter that is slightly less than the interior diameter of the outer sleeve 14 so that they can be easily inserted into the sleeve.

The disclosed NdFeB magnets are of rather recent creation in the magnet art, having first become commercially available in 1984. They are generally regarded as the most powerful "rare-earth" permanent magnet composition commercially available today. "Permanent" in this context means that the material "remembers" the magnetic field to which it has been subjected. Therefore, once the "permanent" magnetic material has been subjected to a sufficient strong magnetic field, the material becomes and stays "magnetized"—exhibiting a high constant magnetic flux even in the absence of an exciting magnetic field or current—unless and until it is subjected to a similarly strong opposing magnetic field. These NdFeB magnets exhibit the highest or among the highest magnetic characteristics of Maximum Energy and Remanence of any commercially available material. For example, NdFeB magnets can provide 4-5 times as much power output (e.g., 28 MGOe to 50 MGOe) as similarly sized ceramic magnets. And because Neodymium is one of the most plentiful so-called "rare earth" elements, and because Iron and Boron are very plentiful, these magnets provide excellent cost-performance ratios.

NdFeB magnets are, however, difficult to manufacture (typically requiring that the powdered material be sintered in a mold), are quite brittle, are difficult to machine, and can be sensitive to corrosion and high temperatures. Nevertheless, their strength vs. size ratio makes them the preferred choice in this invention. They are commercially available in many sizes and shapes from several suppliers around the world, many of whom can be located on the Internet by searching the term "NdFeB magnets." Any of the commercially available grade magnets, such as N33 through N50, are acceptable and can be utilized.

It is not necessary that the relative sizes of the first and second magnets 20 and 24, and the intermediate carbon steel, be precisely as shown in FIG. 2. While it is generally preferred (but not required) that the two magnets 20 and 24 be of about the same size and hence power, the size of the intermediate carbon steel section 22 can be of a significantly smaller size than is depicted in FIG. 2. For example, as shown in FIG. 2, each of the two magnets 20 and 24, and the carbon steel section, are each slightly less than 1 inch in length. The length of the magnets 20 and 24 can be significantly increased (up to approximately 1.2 inches in length or even longer); with the steel segment being respectively shorter.

As also shown in FIG. 2, a pair of simple springs 26 and 28 can be used to hold the magnet/steel assembly stationary within the outer casing 12. Although is not absolutely necessary that the magnet/steel assembly remain stationary, that is preferred. Also, although this preferred embodiment uses springs to do so, there are of course countless other ways to keep the magnet/steel assembly stationary. For just a couple examples, the overall assembly length could be designed to occupy the entire length of the sleeve portion 14, such that the interior peripheral edge of the end caps 16 and 18 act as "stops;" or other compressible material could also be used instead of the springs 26 and 28.

To construct the preferred embodiment, one of the end caps 16 and 18 is welded onto one end of sleeve 14. The spring 26 (or other compressive material of appropriate size, if used) is then inserted. The assembly of the magnet 20, the steel section 22 and the other magnet 24 are then inserted into the sleeve 14 in that order and against the spring 26 in the now-welded end cap 16. The remaining spring 28 is inserted into the other end cap 18, which is welded to the other end of the sleeve 14. The overall exterior is then sanded and polished to a smooth and bright finish, and the device is subjected to a sufficiently strong magnetic field so that the interior magnets 20 and 24 are magnetized to the desired polarity.

Figure 3:
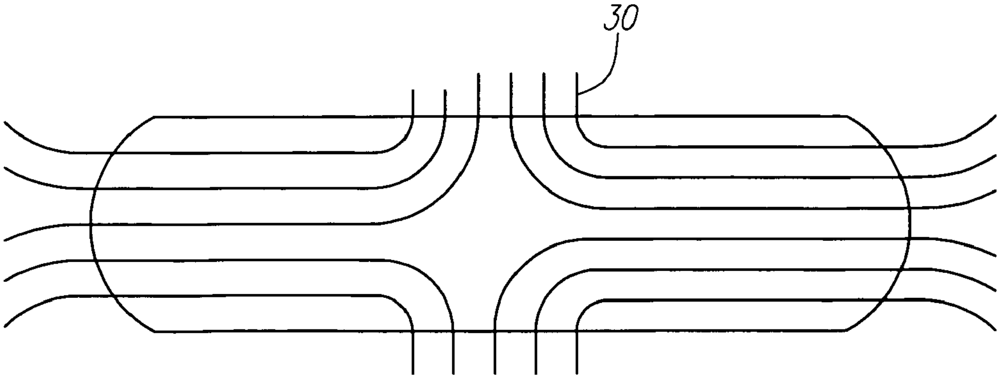
FIG. 3 shows the flux lines for the embodiment shown in FIG. 2.
Figure 4:
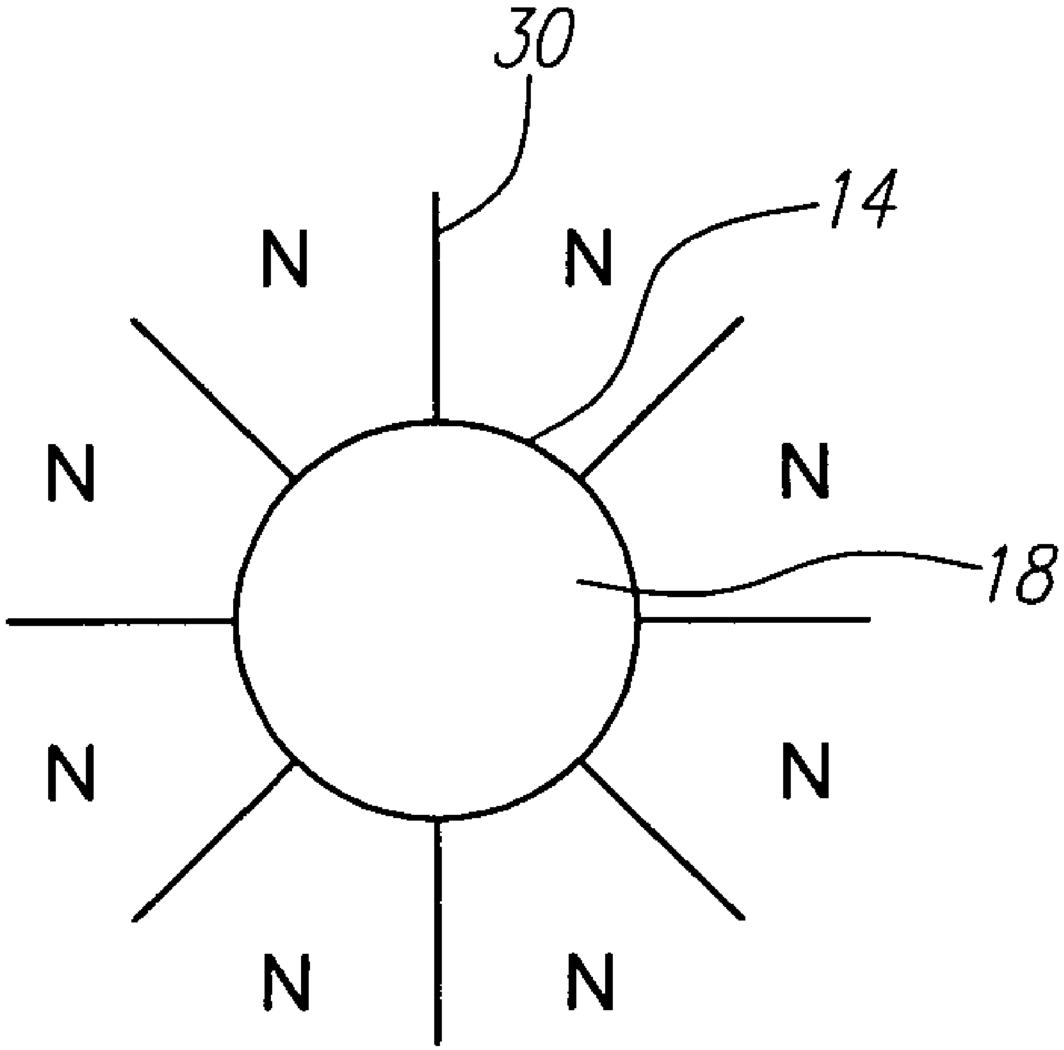
FIG. 4 is an end view showing the radiant magnetic flux orientation of the magnet.

The resultant magnetic flux lines 30 are shown in FIG. 3. It will be noted that the polarity is the same at the ends and the middle of the device, such that the magnetic field radiates around the entire device, as shown in FIG. 4. Although the N polarity is shown in FIG. 4, it will be understood that a S polarity could be achieved as well by reversing the magnetic field by which the overall device is magnetized after construction.

The device of this invention can be easily administered to a cow using the usually pill or bolus apparatus. Once administered, the animal pill magnet remains in the cow's stomach were it will collect and hold a large amount of tramp iron.

Although preferred embodiments have been shown and described, the disclosed invention and the protection afforded by this patent are not limited thereto, but are of the full scope of the following claims, and equivalents thereto.

What is claimed is:

1. An animal pill magnet for the treatment of hardware disease in bovine animals, the animal pill magnet comprising:

a) a casing comprising a sleeve and end caps;

b) at least a pair of NdFeB magnets housed within said casing, separated by a section of carbon steel;

c) such that the resultant magnetic field at both ends of the magnet is of a single polarity; and d) a pair of springs, one each in each said end cap.

2. The invention of claim 1 in which the length of said magnets on either side of said carbon steel section is substantially the same.

3. The invention of claim 1 in which the length of said magnets on either side of said carbon steel section, and the length of said carbon steel section are substantially the same.

4. The invention of claim 2 in which said carbon steel section is smaller in length than is the length of said magnets on either side thereof.

5. The invention of claim 1 wherein said end caps are welded onto said sleeve.

6. An animal pill magnet for the treatment of hardware disease in bovine animals, the animal pill magnet comprising:

a) a casing comprising a sleeve and end caps;

b) at least a pair of NdFeB magnets housed within said casing, separated by a section of carbon steel;

c) such that the resultant magnetic field at both ends of the magnet is of a single polarity, and d) means placed in each end cap for biasing said magnets toward the middle of the animal pill magnet.

7. The invention of claim 6 in which said sleeve is substantially cylindrical in exterior shape.

8. The invention of claim 6 in which said end caps are substantially semi-hemispherical in shape.

9. The invention of claim 6 in which said sleeve is constructed of stainless steel.

10. The invention of claim 9 in which said end caps are constructed of stainless steel.

11. The invention of claim 10 in which said end caps are attached to said sleeve by welding.

* * * * *